US00PP21708P3

(12) United States Plant Patent
Sproul

(10) Patent No.: US PP21,708 P3
(45) Date of Patent: Feb. 15, 2011

(54) ROSE PLANT NAMED 'SPROIMPRESS'

(50) Latin Name: *Rosa hybrida*
Varietal Denomination: SPRoimpress

(75) Inventor: James Sproul, Bakersfield, CA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 164 days.

(21) Appl. No.: 12/322,885

(22) Filed: Feb. 9, 2009

(65) Prior Publication Data

US 2010/0205700 P1 Aug. 12, 2010

(51) Int. Cl.
*A01H 5/00* (2006.01)

(52) U.S. Cl. ..... Plt./134; Plt./118

(58) Field of Classification Search ..... Plt./118, Plt./134
See application file for complete search history.

(56) References Cited

U.S. PATENT DOCUMENTS

PP6,725 P * 4/1989 Warriner ..... Plt./137
PP9,389 P * 12/1995 Winchel ..... Plt./132
PP17,873 P3 * 7/2007 Sproul ..... Plt./128

* cited by examiner

*Primary Examiner*—Wendy C. Haas

(57) ABSTRACT

This new rose plant bears dark yellow, fully double, hybrid tea form flowers that open to 3 inches and more across, from late spring to late fall. It is a medium sized plant with upright growing habit, having very good resistance to powdery mildew.

1 Drawing Sheet

Genus and species: This present invention is a new variety of *Rosa hybrida.*

Varietal denomination: This new cultivar has the varietal denomination of 'SPRoimpress'.

CROSS REFERENCE

This new invention is a unique cross from this breeding program. The seed parent, a seedling of 'WEKjoe' (U.S. Plant Pat. No. 9,389) by 'JACient' (U.S. Plant Pat. No. 6,725), was a pink blend, large-flowered, hybrid tea type rose, used in several previous crosses, also as the seed parent. Of these, only one has been introduced, 'SPRoheather' (U.S. Plant Pat. No. 17,873), a pink flowered rose of the miniature class. 'SPRoheather' and 'SPRoimpress' are both upright-growing roses and have similar, fully-double flower form and good resistance to powdery mildew. 'SPRoimpress', can be easily distinguished from 'SPOheather' by size and color. 'SPRoimpress' has larger and dark yellow flowers, usually opening to 3 or more inches across, and medium-green glossy foliage; 'SPRoheather' has pink flowers that open to not more than 2¾ inches across, dark-green, semi-glossy foliage, and is registered in the miniature rose class. This new invention would better fit into the Mini-Flora class.

BACKGROUND OF THE INVENTION

This new and distinct variety of rose was produced by James A. Sproul, under conditions of careful and controlled observation, at his nursery in Bakersfield, Calif. It is the result of crossing two seedlings from his breeding program: 'WEKjoe' (U.S. Plant Pat. No. 9,389) by 'JACient' (U.S. Plant Pat. No. 6,725) as seed parent; and 'WEKblusi' (U.S. Plant Pat. No. 10,188) by 'SCRivluv' (unpatented), as pollen parent. This new invention has been given the trade name of FIRST IMPRESSION.

The primary objective of this breeding was to produce new rose varieties with superb resistance to diseases, especially powdery mildew, and with an abundance of flowers. Hybrid tea flower form was also a goal. To meet this objective, parents were chosen for their proven resistance to powdery mildew and abundance of bloom with good flower form, with the intention of crossing them directly with 'SCRivluv' or seedlings of 'SCRivluv', which is noted for it's superb resistance to black spot. The objective was substantially achieved in this new, dark yellow rose that has hybrid tea form buds and flowers on a plant continually in bloom and that is proving its ability to resist diseases.

The seed parent is a seedling from this breeding program, 'WEKjoe' by 'JACient'. It was a pink blend, large-flowered, hybrid tea type rose. 'SPRoimpress', is easily distinguished from its seed parent by color of flowers and size and habit of the plant. By way of comparison, 'SPRoimpress' has dark yellow flowers, borne in clusters, and is shorter and more branched. Being a hybrid tea rose, the flowers of the seed parent are borne primarily singly.

The pollen parent, 'WEKblusi' by 'SCRivluv', also has yellow flowers but they are a lighter yellow, smaller in size and with fewer petals. It has been used within this breeding program as pollen parent for a number of crosses, still being evaluated. The resulting offspring are also yellow but had yellow roses as seed parents. Some of these offspring show traits similar to the flower form and disease resistance of this new invention but none has the same upright plant habit or flowers of as dark a yellow.

BRIEF SUMMARY OF THE INVENTION

This present invention relates to a new and distinct cultivar of hardy, bush type rose plant, which has several features that distinguish it from other presently available roses, of which I am aware. Among these characteristics are its unique combination of the following:

- the dark shade of yellow of the flowers;
- the length of time these flowers hold their dark yellow color;

those flowers borne primarily in small clusters of 2 or 3;
the fully double, hybrid tea form of those flowers;
the slight to moderate fragrance of those flowers;
its near continuous blooming habit;
its upright plant habit, growing 24 to 42 inches tall;
its medium green, glossy foliage;
its above average resistance to powdery mildew;
its ability to root easily from cuttings.

Subsequent to the origination of the cultivar, it was successfully asexually reproduced in Bakersfield, Calif., by budding on to 'Dr. Huey' (not patented) rootstock, and in Arroyo Grande, Calif., by cuttings. The reproductions have run true in all respects.

BRIEF DESCRIPTION OF THE DRAWING

The accompanying color photograph show a plant that had been grown in a greenhouse in Arroyo Grande, Calif. The larger image, taken on April 19, shows foliage, buds and flowers of this new cultivar in different stages of development on a four year old plant. The smaller inset image, taken a week later, is a close-up of peduncles and buds on this same plant, showing the anthocyanin coloration that was present.

BOTANICAL DESCRIPTION OF THE PLANT

Unless otherwise noted, the following observations, measurements, values and comparisons are from a four-year-old plant of *Rosa hybrida,* 'SPRoimpress', as grown outdoors in Ipswich, Mass. The plant arrived in April, in a 10-inch plastic nursery container, growing in an artificial soil mix. In July, 2008 it was transplanted into a five gallon bucket, with drainage holes, in a peat moss and compost mix. Observation was continued through October. Phenotypic expression may vary with environmental, cultural, and climatic conditions. Color references are made using The Royal Horticultural Society Colour Chart, except where common terms of color are employed.

FLOWERS

BLOOMING HABIT: This new cultivar bears its flowers mostly in clusters of 2 to 3, but also singly. Flowers opened slowly, taking eleven days to fully open. The dark yellow color lasted for an additional 5 to 7 days. By the time one flower in a cluster is fading, one or two others in the same cluster were starting to show their color, so the mature plant usually always had some flowers showing the dark yellow color.

BUD form is broadly ovate with a truncated base and acute apex. Diameter varies from 13/32 inch to 17/32 inch with a length varying from 17/32 inch to 23/32 inch.

BLOOM size varied from 2 15/16 to 3 11/16 inches across and often was not symmetrical with cross diameters differing by 1/8 to 1/4 inch. Profile depths of the flowers varied from 1 1/16 to 2 1/4. The bloom opens with a flat upper profile and cupped lower profile. The flower takes about 11 days to full open stage. Full open the upper profile is convex and the lower profile is arcuate. Petalage was around 40 with 7 or 8 petaloids. The outer 20 to 25 petals are arranged shingle-like; inner petals may be still attached shingle-like but the petals themselves may be wrapped around each other, curling tightly into the middle of the flower. Petaloids are at the center of this whorl. Fragrance is slight to moderate.

PETALS are of medium thickness, with very good substance. The texture of the adaxial surface was glabrous and somewhat satiny. Veins radiated from the base of the petal and were somewhat recessed. The abaxial surface began satiny and became slightly coarse. These veins were also recessed. The shape of the outer petals was very broad spatulate. The outer margin was arcuate, with a very shallow notch on each side of an acute tip at the apex. The intermediate petals were obovate with a cordate base, a rounded margin and had a more pronounced notch on either side of the apex, to the point where one petal was mitten-shaped. Inner petals had an arcuate margin that was ruffled around the apex. The outer margins reflex slightly as the petals unfurl, with the reflex increasing as the bloom opens. Petals on the full open bloom appear somewhat quilled.

COLOR is a dark yellow, which usually has slight orange tones in full summer sun. In these color comparisons, this first paragraph is the colors observed from plants directly from a greenhouse. The second paragraph is the darkest color observed in full summer sun.

The first color visible when the sepals divided was a dark yellow, near 7C. During the first few days, the color of the adaxial surfaces of the outer petals was shades of dark Aureolin Yellow, between 12A and 12B, and near 7D along the margins. The basal area and point of attachment were near 12A. The abaxial surface was a Lemon Yellow, near 13B with near 12D along the margins, and often a very light blushing and/or streaking of a dark red, near 181C, on the outermost petals where they were first exposed to the sun. The basal area was a Lemon Yellow, between 13A and 13B. The adaxial surface of the inner petals was near 12A, becoming between 12A and 12B toward the margins. The basal area and point of attachment were near 12A. The abaxial surface of the inner petals was between 13A and 12A with near 13A in the basal area and point of attachment. When half blown, the adaxial surface of all petals was a bit lighter, between 10B and 9B, with a basal area near 9B. The reverse of all petals was near 13B, including the basal area. When full blown, all petals were near 12A on the adaxial surface with a basal area between 12A and 13B. The reverse of all petals was near 13C with between 12B and 13B in the basal area.

In full summer sun, the first color visible when the sepals divided was a dark Canary Yellow, near 9A. During the first few days, the color of the adaxial surfaces of the outer petals was shades of a dark yellow, between 12A and 14B. The basal area was near 12A. The point of attachment was a dark Canary Yellow, near 14B. The abaxial surface was near 14A, with a light blushing and/or streaking of a dark red, near 181C, on the outermost petals where they were first exposed to the sun. The basal area was near 14B and the point of attachment was near 14A. Inner petals were the same except the point of attachment of the adaxial surface was near 14A. When half blown, the adaxial surfaces of the outer petals were still between 12A and 14B, except the area along the margins, had become a Lemon Yellow between 13A and 13B. The basal area was near 13B and the point of attachment was near 13A. Reverse of these petals was unchanged. The inner petals had lightened to a Canary Yellow near 9A with a very dark orange-yellow, near 17A, at the point of attachment which blended into the petal in the basal area. The reverse had lightened a little to between 12A and 12B and with near 17A at the point of attachment. When full blown the adaxial surface of the outer petals had become near 9C. The basal area and point of attachment was near 9B. When half open, the adaxial surface or the outer petals was between 12A and 12B, occasionally having various sized blotches of near 12D in the upper one-third to one-fifth of the petal, and margins between 13A and 13B. The basal area was near 13B and the point of attachment near 13A. The inner petals were near 9A with near 17A at the point of attachment that blended up into the near 9A in basal area. The reverse of all petals was near 12A with near 17A at the point of attachment. When full blown, the upper surface of the outer petals was near 9C, and became near 4C toward the margins. The basal area was near 9B. The inner petals were near 7D on the adaxial surface and near 9B in the basal area. The reverse of all petals was near 9C with the main veins appearing near 9B.

PETALOIDS were the same color and texture as the inner petals. They were found to vary in widths from 4/16 to 13/16 inch and in length from 7/16 to 1 1/8 inches, not respective to width. They were often cleft, varying from barely cleft to deeply cleft. The bases were generally quite narrow and occasionally attached to the receptacle by a filament. There were often anthers or partial anthers attached at some point along the main vein, which was often found at the top or along one side of the petaloid. A few of the stamens appeared virile. The smallest petaloids were tightly adjacent to the stamens.

SEPALS: The flower has five sepals, permanently attached to the receptacle. Just before the sepals divide, they extend beyond the tip of the bud by 7/16 to 1/2 inch. Their form was ovate with apiculate apices and truncated bases. The margins were ciliate and the three outer sepals had none to one spindleate foliar appendage along each margin. Lengths varied from 31/32 to 1 3/16 inches and widths varied from 11/32 to 16/32 inch. Outside surfaces were semi-glossy in the center and became matte along the margins. There were many stipitate glands with the gland itself being near 183C, an Oxblood Red. The center of the outside surfaces was a medium yellow-green, between 144A and 146B; along the margins was a bit darker, near 146B; and all were flushed near 176B with some areas near 183C along the margins. Inside surfaces were near 148A and had a fine, even pubescent coating. Areas that were near 183C on the outer surface showed through as near 183D. Sepals reflexed back well ahead of the petals, and the two outermost sepals crossed over the peduncle with the rest of the sepals curled back and up so the tips were near the receptacle. They were permanently attached to the receptacle.

The RECEPTACLE was conical, truncated at the top, and the base was tapered to connect evenly to the peduncle. The diameter near the top was between 5/16 and 6/16 inch. The diameter where it connects to the receptacle varied from 7/64 to 10/64 inch. The height varied from 4/16 to 5/16 inch. The surface was smooth and glossy, a medium yellow-green, near 144A, and with a fine fuzzy coating.

PEDUNCLES were strong and straight. The surface was glossy when young and became matte when old. The color was a light yellow-green, near 145B, when young, became near 145A and then near 144A as the hip formed. Anthocyanin flushing was usually strong, a browned-red near 178A, on the sunward side, which disappeared as it aged. There were hairs, and numerous stipitate glands of an Oxblood Red, near 183C, when young and became near 176A as the hip began to form. The diameter of all the peduncles averaged 1/8 inch, averaging 7/64 inch right below the receptacle, tapering down to 6/64 inch and then up to 9/64 inch where it connected to the stem. When there were two buds in a cluster, peduncles varied in length from 1 13/32 to 2 10/32 inches. When borne three to a cluster, peduncles varied in length from 1 1/4 to 1 11/16 inches.

REPRODUCTIVE ORGANS

ANDROCIUM: Stamens are arranged around the outer edge of the receptacle. About 117 was the most common quantity noted. The color of the ANTHERS was a pale yellow, near 13D. Pollen sacs were much darker, an Indian Yellow near 17A. FILAMENTS were found to be straight in the half open flower and undulant in the full open bloom. Lengths varied from 2/16 to 5/16 inch, but lengths within a single flower only varied by 1/16 to 1/8 inch. Their color was a Lemon Yellow, near 13A.

GYNOECIUM: PISTILS originated in the center of the top of the receptacle. There were around half or less as the number of stamens. The STYLES were very thin, straight and covered with hairs. Length varied from 3/32 to 9/32 inch, varying as much as 1/8 inch within a single flower. The color was a very light Primrose Yellow, near 4D. STIGMAS were wide, about 1/32 inch across, and were a dull yellow-green color near 160A.

HIPS may be nearly round and truncated at the top or may have a broad urn-shaped profile. Both forms were found within the same clusters. Sepals remained permanently attached and recurved along the hip but generally not tight against the hip. Overhead views revealed circumferences usually were not symmetrically rounded, with diameters averaging 7/8 inch, ranging from 12/16 to 15/16 inch and differing on each hip from none to 3/32 inch. Height of all hips varied from 6/8 to 7/8 inch. The color when the hips are mature was a deep orange, between 169A and 169B, becoming less orange at the base, near 167A. SEEDS often protruded from the top, though sometimes they were only barely visible. The portion of the seed that was protruding was a dark brown, between 200A and 166B.

PLANT

PLANT HABIT was upright and quite vigorous, growing 24 to 42 inches tall and 24 to 38 inches wide. Flowers were borne 2 to 4 to a cluster on stems that were 9 to 12 inches long. The diameter of main canes was 5/16 inch and of flowering stems was 3/16 inch. The surface of new growth was glossy and glabrous. The color was near 144B with the sunward side flushed slightly with near 175A. Old wood was semi glossy and glabrous. The color was a darker green, between 144A and 146A.

FOLIAGE was pinnately compound, usually with seven leaflets but occasionally with five or three or even nine. There were usually four to six leaves per flowering stem, not including the one or two stipilate appendages at the juncture with the peduncle, and regardless of the length of the stem. Leaflets closest to the base of the leaf were orbicular, becoming less so and more broadly oval, progressing up the rachis, until the terminal leaflets were broadly ovate. The base was rounded, the apex was acute. Serration was a simple, near even, medium serration. The adaxial surface was glossy and glabrous with main and primary lateral veins recessed. The reverse was leathery when young and became coarse when mature. The main veins were protruding entirely, primary lateral veins protruding less and secondary lateral veins barely protruding. Mature leaves were 4 5/16 to 5 7/8 inches long. Terminal leaflets were 1 1/16 by 1 27/32 inches wide and 1 11/32 to 2 5/16 inches long, with length somewhat relative to width.

COLOR of the adaxial surface of the new foliage was a Lettuce Green, near 144A, with margins of a copper-brown, near 175A, that blushed inward from the margins. The abaxial surface was a Scheele's Green, near 144B, blushed with near 175A, fading as it progressed inward from the margins. Older foliage was darker than a color between 139A and 147A. The reverse was darker than a color between 137A and 191A with veins a very light green, near 145C.

PETIOLES on the adaxial surface of the young foliage appeared near 175A along the ridges and near 144D in the groove, lightly flushed with near 175A and even less of a blush between the stipules. The older foliage was near 143C in the groove of the adaxial surface, with a thin line along the ridge that was the same color as the adjoining leaflet blade. The abaxial surface was near 144B. The length of the petioles varied from 22/32 inch to 27/32 inch, with the shorter petiole on the seven-leaflet leaves.

The RACHISES and PETIOLULES were the same color as the petioles, except there was heavier flushing on the petiolules on the young foliage. Lengths of the rachises varied from 1⅛ to 2⅛ inches, with the longest rachises on seven leaflet leaves. Lengths of petiolules to the terminal leaflet varied from 14/16 to 1 9/16 inches. The length of the petiolules to the other leaflets varied from 2/32 to 3/32 inch.

STIPULES were paired at the base of the petioles. They were laying flat with a dentate margin. On mature leaves they were measured from 9/16 to 13/16 inch attached and 3/16 to 4/16 angled outward at a 40° angle. The part angled outward was attenuate. The color on the adaxial surface was near 137B and the abaxial surface was near 137C.

PRICKLES quickly tapered to a long and slender point and were slightly arcuate. On main canes they were found to be 10/32 inch long. On the flowering stems, lengths varied from 7/32 to 15/32 inch, with the shorter prickles toward the base of the stem. In the first inch of stem from the base, no prickles were found, and there were two in three inches of stem. Further up the stem there were four to six in five inches of stem. The color when young was a medium browned-purple, near 183D, on the upper side and near 144A on the lower side. When old the entire prickle was near 165B, an almond shell brown.

RESISTANCE: 'SPRoimpress' has demonstrated great resistance to powdery mildew, blackspot and downy mildew in Massachusetts. In California, it was found to be resistant to powdery mildew and rust but susceptible to blackspot. In Massachusetts, it also showed good resistance to insects, in particular, aphids and rose midge.

HARDINESS: 'SPRoimpress' has proven hardy through testing in USDA zones 5 through 9.

The invention claimed is:

1. A new and distinct variety of rose plant is claimed, substantially as described and illustrated herein.

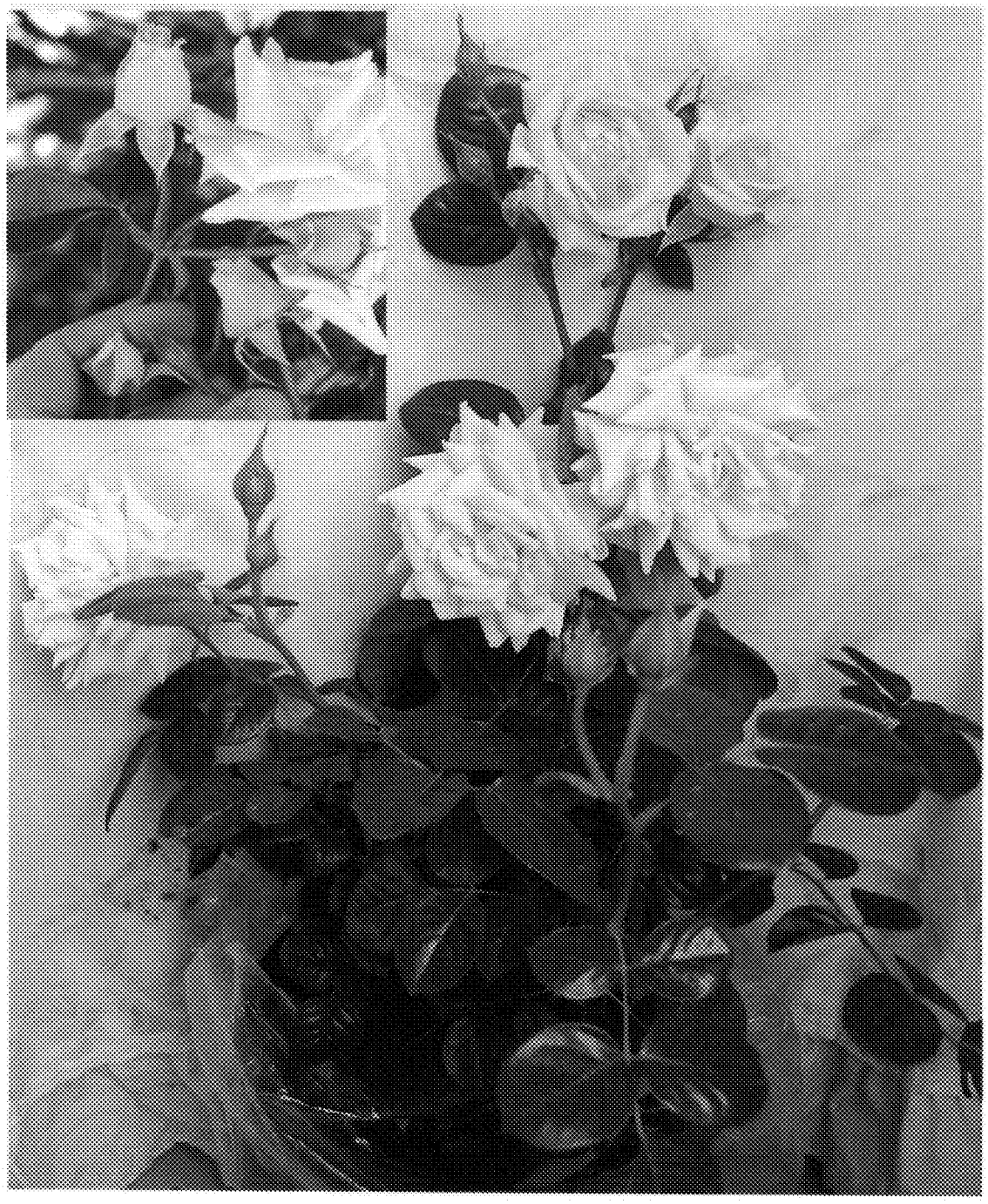

* * * * *